United States Patent [19]

Kamitani

[11] Patent Number: 4,896,380
[45] Date of Patent: Jan. 30, 1990

[54] FACE MASK EQUIPPED WITH EARPLUGS

[76] Inventor: Shigeki Kamitani, 8-1-933, Nakahara 1-chome, Isogo-ku, Yokohama-shi, Kanagawa-ken, Japan, 235

[21] Appl. No.: 296,780
[22] Filed: Jan. 13, 1989
[30] Foreign Application Priority Data Jul. 22, 1988 [JP] Japan .................................. 63-97002

[51] Int. Cl.⁴ .............................................. A61F 9/02
[52] U.S. Cl. ........................................ 2/428; 128/864
[58] Field of Search .................. 2/428, 429, 430, 426, 2/209; 128/866, 867, 865, 864, 868

[56] References Cited

U.S. PATENT DOCUMENTS 2,488,235  11/1949  Pfeiffer ...................................... 2/428
3,110,356  11/1963  Mendelson ...................... 128/865 X
4,219,018   8/1980  Draper, Jr. ........................... 128/864
4,406,282   9/1983  Parker et al. ........................ 128/865

Primary Examiner—Peter Nerbun
Attorney, Agent, or Firm—Cushman, Darby & Cushman

[57] ABSTRACT

Disclosed is a facemask equipped with earplugs which permits wearers to hear clearly sounds underwater or hear others to speak to each other. The earplugs can be easily removed from their ears after finishing scuba diving. Thus, scuba diving will increase fun. As a matter of course, wearers will not suffer from bradyacusia, and they will have no fear of losing the sense of balance by allowing cold water to reach the semicircular canals of the inner ear while swimming underwater.

2 Claims, 1 Drawing Sheet

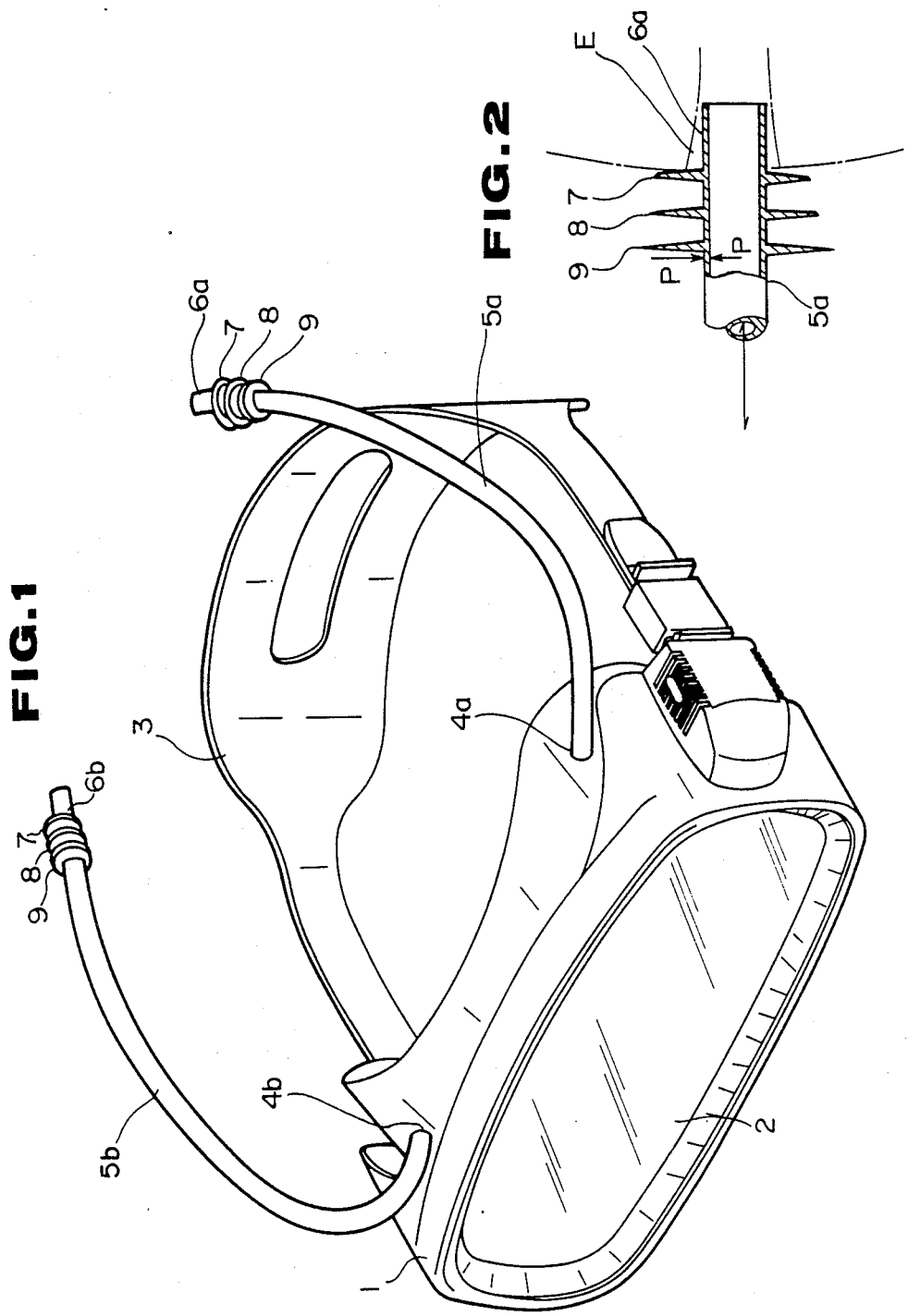

FACE MASK EQUIPPED WITH EARPLUGS

BACKGROUND OF THE INVENTION

1. Field of the Invention

The present invention relates to a face mask which is designed to be used underwater in scuba diving, comprising a mask body to closely fit a face to cover the eyes and nose, or the entire face, particularly to such a face mask equipped with ear plugs.

2. Description of the Prior Art

Scuba diving is very popular. Scuba divers have an inclination to use to ear stoppers to close their ears. Then, water will come in and out of ear holes until the pressure within the ear holes and the water pressure at the water depth balance. This will be a cause for bradyacusia. Also, there is a fear of breaking eardrums. Assume that eardrums are broken in the water, the cold water reaches the three semicircular canals of the inner ear, thereby causing the diver to lose the sense of balance. As a result the diver cannot make a decision as to which is upside or downside, and this is a dangerous situation. To deal with this it appears to suffice that scuba divers use earplugs. When they dive deep to swim underwater, the earplugs will be pushed so deep into their ears under the influence of water pressure that it is difficult to remove the earplugs from their ears.

For fear of this, in fact, scuba divers do not want to use earplugs.

Also, when they use earplugs, they cannot hear any sounds underwater, and they cannot have a pleasure of hearing sounds underwater or speaking to each other unless such sounds or voices are extraordinarily loud.

SUMMARY OF THE INVENTION

With the above in mind one object of the present invention is to provide a face mask equipped with earplugs which permit the wearer to hear clearly sounds made underwater or hear others to speak to each other, while assuring that the earplugs can be easily removed from the ears after scuba diving. Thus, scuba diving will be more fun. As a matter of course, wearers will not suffer from hardness of hearing, and they will not lose their sense of balance while swimming underwater.

To attain this object a face mask according to the present invention comprises a mask body to closely fit a face to cover at least eyes and nose, a piece of glass or transparent plate, and two tubes extending from the mask body and communicating with the closed space within the mask body, each tube being terminated with an earplug. According to a preferred embodiment of the present invention each ear plug has a plurality of annular flanges arranged longitudinally and integrally connected to the tube. The mask body may be large enough to cover the entire face of scuba diver. Air will come out in the closed space of the face mask through the diver's nose, and then the air reaches his ears through the tubes. The air stored in his lungs is kept at the same pressure as the water pressure at the depth at which he swims underwater. Therefore, the pressure in the ear holes and the water pressure balance, no matter how deep the scuba diver may dive and swim underwater. The earplugs cannot be collapsed or pushed deep into the ear holes, thus assuring that they can be used safely.

When sounds are made underwater, they will cause the lens of a face mask to resonate, and then the air trapped in the closed space of the mask body will vibrate accordingly for the sounds and will reach the diver's ears via the tubes. The sound-receiving area of the face mask lens can be increased to its limit by directing the lens towards the sound source. Thus, the sounds can be heard clearly. Wearing the earplugs assures that scuba divers will not suffer from hardness of hearing and will not lose their sense of balance.

Other objects and advantages of the present invention will be understood from the following description of a face mask according to a preferred embodiment of the present invention:

FIG. 1 is a perspective view of the face mask; and

FIG. 2 is a longitudinal section of an earplug of the face mask.

EMBODIMENT

FIG. 1 shows a face mask which is designed to cover the eyes and nose of a scuba diver, but it should be understood that the present invention can be equally applied to a face mask which is designed to cover the entire face. In FIG. 1 a mask body 1 has a transparent plate 2 made of, for instance, glass. When a scuba diver wears the face mask, it will cover his eyes and nose to define a closed space which is filled with air in the face mask 1. Straps are indicated at 3.

A pair of tubes 5a and 5b are fixed to the opposite sides 4a and 4b of the mask body, and these tubes are long enough to reach the ears of an wearer to permit his ear holes E to communicate with the space which is defined by the mask body 1 and the lens 2. As shown, each tube has an earplug at its end 6a or 6b.

The tube size may be arbitrarily selected, but its end size should be selected to closely fit in the ear hole E. In this particular embodiment each earplug has a plurality of annular flanges 7, 8 and 9 longitudinally arranged and integrally connected thereto. These annular flanges are used to prevent invasion of water into ear hole E, and they may be smaller diameters towards the end of the tube.

When a scuba diver wears this face mask to cover his eyes and nose with its tube ends inserted in his ears, each tube has the same pressure P applied thereto as the water pressure at the depth at which he dives and swims underwater.

The air stored in his lungs enters his ear holes through his nose and the tubes 5a and 5b. The air has the same pressure as the water pressure at the depth at which he dives and swims underwater. Therefore, the earplugs 6a and 6b cannot be collapsed. They cannot be pushed into the ear holes either, thus assuring that the earplugs are safely used. When a sound is produced in water, it will reach the tubes to vibrate the air inside, thereby permitting the wearer to hear the sound. Also, the sound will reach the lens 2 of the face mask to vibrate the air inside. The diver can hear the sound well by directing the lens towards the sound source to increase the sound receiving area of the lens. Thus, the wearer can have much fun in scuba diving.

The annular flanges 7, 8 and 9 will prevent invasion of water into the ear holes of a wearer, and at the same time they will make it easy for the earplugs to closely fit in his ear holes E.

A generally "Y"-shaped tube may be used in place of two tubes 5a and 5b. Also, each earplug may have a stopper to close its open end while not used.

As may be understood from the above, a face mask equipped with earplugs according to the present invention permits wearers to hear clearly sounds underwater or hear others to speak to each other. The earplugs can be easily removed from their ears after finishing scuba diving. Thus, scuba diving will increase fun. As a matter of course, wearers will not suffer from hardness of hearing, and they will not lose the sense of balance while swimming underwater.

What is claimed is:

1. Face mask which is designed to be used underwater comprising:

a mask body configured to closely fit a face so as to cover at least the eyes and nose, and a piece of glass or transparent plate, first and second tubes extending from the mask body and in free flowing fluid communication with a closed space defined between the mask body and the face, each said tube having an open end remote from the mask body which is sized and shaped so as to be insertable into an ear canal, said remote end of each tube having a plurality of annular flanges disposed longitudinally thereof and integrally with said tube.

2. Face mask according to claim 1 wherein said mask body is large enough to cover the whole size of a face.

* * * * *